United States Patent [19]

Pesa et al.

[11] 4,312,781

[45] Jan. 26, 1982

[54] PROCESS FOR THE SEPARATION OF CATALYST FROM PRODUCTS OBTAINED IN THE HYDROCARBOXYLATION OF UNSATURATED NITRILES

[75] Inventors: Frederick A. Pesa, Aurora; Thomas A. Haase, University Hts., both of Ohio

[73] Assignee: Standard Oil Company, Cleveland, Ohio

[21] Appl. No.: 175,804

[22] Filed: Aug. 6, 1980

[51] Int. Cl.[3] .................... B01J 31/40; C07C 121/38; C07C 121/407

[52] U.S. Cl. .................... 252/414; 260/465.1; 260/465.4; 260/465.6; 568/455

[58] Field of Search .................... 252/414, 431 N; 260/465.4, 465.1

[56] References Cited

U.S. PATENT DOCUMENTS

| | | | |
|---|---|---|---|
| 3,856,832 | 12/1974 | Ethyl | 252/414 |
| 3,996,164 | 12/1976 | Matsuda | 568/455 |
| 4,041,057 | 8/1977 | Fanning | 560/233 |
| 4,141,915 | 2/1979 | El-Chahawi et al. | 260/465.4 |
| 4,209,467 | 6/1980 | Kojima et al. | 252/431 N |

FOREIGN PATENT DOCUMENTS

| | | | |
|---|---|---|---|
| 1344669 | 1/1974 | United Kingdom | 260/465.4 |
| 1497046 | 1/1978 | United Kingdom | 260/465.4 |

*Primary Examiner*—P. E. Konopka
*Attorney, Agent, or Firm*—Salvatore P. Pace; Herbert D. Knudsen; Larry W. Evans

[57] ABSTRACT

A process is provided which includes the separation of a hydrocarboxylation-type catalyst together with the hydrocarboxylation solvent from a reaction mixture containing an oxygenated cyanocompound product, the hydrocarboxylation catalyst and the hydrocarboxylation solvent by contacting the reaction mixture with a hydrocarbon to form a hydrocarbon/solvent conjugate phase, and separating the resulting hydrocarbon phase from the solvent phase.

50 Claims, No Drawings

PROCESS FOR THE SEPARATION OF CATALYST FROM PRODUCTS OBTAINED IN THE HYDROCARBOXYLATION OF UNSATURATED NITRILES

BACKGROUND OF THE INVENTION

This invention relates to the separation of reaction products and of active catalysts from hydrocarboxylation reaction mixtures. More particularly, the present invention relates to the separation of oxygenated cyanocompounds and of active cobalt and/or ruthenium carbonyl catalysts, with promoters, from hydrocarboxylation reaction mixtures.

Conventional methods of separating reaction products and reaction catalysts from reaction mixtures include distillation and catalyst precipitation. The major products from the hydrocarboxylation of nitriles, that is, oxygenated cyanocompounds, have very high boiling points with respect to the hydrocarboxylation catalysts, generally cobalt and/or ruthenium carbonyl, which are rather heat sensitive. To separate these products by distillation would cause the deactivation and degradation of a significant portion of the catalyst present in the reaction mixture. The catalyst would then require reformation and reactivation before it could be recycled for further use in the reaction. The separation of reaction products by precipitation of catalysts also results in the necessity of reactivating the catalyst before recycle.

U.K. Pat. No. 1,344,669; U.S. Pat. Nos. 3,856,832 and 4,041,057 disclose the extraction of the ester product of a cobalt catalyzed hydroesterification reaction using a hydrocarbon having a boiling point above 70° F. resulting in an ester-containing hydrocarbon phase, and a catalyst-containing alkanol phase. A pyridine promoter is present in both phases, and the catalyst is in an active form for recycling.

Japanese patent application No. 75 62,888 discloses the recovery of catalysts used in esterification of alcohols with olefins and carbon monoxide by the addition of aliphatic hydrocarbons to the reaction mixture. U.S. Pat. No. 3,996,164 discloses the separation of pyridine- and substituted pyridine-promoted cobalt carbonyl complexes from hydroesterification media by cooling a hydrocarbon-containing mixture below 80° C. such that the catalyst utilized becomes insoluble and can be separated.

It has been found that when alcohol solvents are used in the reaction mixtures from the hydrocarboxylation of nitriles to form oxygenated cyanocompounds, the conjugate phase separation of the cyanoproduct from the reaction mixture and catalyst is impractical due to the cyanoproduct being more miscible in the alcohol solvent, than in the hydrocarbon extractant.

SUMMARY OF THE INVENTION

It is therefore an object of the present invention to provide a process for the separation of oxygenated cyanocompounds from hydrocarboxylation reaction mixtures.

It is a further object of the present invention to provide a process for the separation of hydrocarboxylation catalysts systems from oxygenated cyanocompounds.

It is a further object of the present invention to provide a process for the separation of hydrocarboxylation catalysts systems from oxygenated cyanocompounds, which catalyst systems remain in an active form during such separation, suitable for recycle in the hydrocarboxylation process.

It is a further object of the present invention to provide a process for the separation of cyanocompounds from ligand-promoted cobalt and/or ruthenium carbonyl catalysts, comprising conjugate phase extraction with hydrocarbons.

In general, the process of the present invention includes the separation of a hydrocarboxylation-type catalyst together with the hydrocarboxylation solvent from a reaction mixture containing an oxygenated cyanocompound product, the hydrocarboxylation catalyst and the hydrocarboxylation solvent by contacting the reaction mixture with a hydrocarbon to form a hydrocarbon/solvent conjugate phase, and separating the resulting hydrocarbon phase from the solvent phase.

DETAILED DESCRIPTION OF THE INVENTION

Conjugate-phase extraction involves the use of two liquids which are at least partially miscible. The presence of a third component in the mixture may cause a decrease in the mutual solubilities of the two liquids. The third component may be preferentially soluble in either one or both of the liquids in the mix.

In the present invention, the catalyst and products of hydrocarboxylation reactions are separated. The hydrocarboxylation reaction mixture or the reactor effluent, containing the reaction solvent, the reaction product, the reaction catalyst and any promoter ligand compounds utilized, is combined with an at least partially miscible extracting liquid to form a two-phase conjugate solution. Generally, one phase comprises substantially the extracting liquid and hydrocaboxylation product, and the second phase comprises substantially the reaction solvent and the active catalyst. The promoter ligand utilized generally is distributed in some proportion between the two phases. The two liquid phases may be recovered according to conventional multiphase separation procedures such as centrifugation and settling.

If a substantial proportion of the product remains in the reaction solvent after a single extracting step, repeated extraction of the product is carried out, either by the addition of substantially the partially miscible extracting liquid or by the addition of the catalyst-containing reaction solvent phase a mixture containing portions of both the extracting liquid and reaction solvent. The addition of the extracting liquid/reaction solvent mixture is preferably utilized when the two phases are not to be recovered after the first extraction. The addition of the mixture permits the relative ratios of the extracting liquid to reaction solvent to remain approximately equal.

The extraction process of the present invention may be carried out in separating oxygenated cyanocompounds from the reaction mixture or reactor effluent of hydrocarboxylation-type reactions such as hydroformylation, hydrocarbonylation, hydroesterification and subsequent processes involving the reaction mix of these reactions.

Oxygenated cyanocompounds which will be separated according to the process of the present invention include the products of the above reactions, preferably cyanocarbonyl compounds including, but not limited to, cyanoacids, cyanoesters, cyanoaldehydes, cyanoacetals, cyanoamides and the like. Representative oxygenated cyanocompounds include, but are not limited to cyanopropionic acid, cyanovaleric acid, the isomers and methyl, ethyl, propyl and butyl esters thereof; cyanopropional, cyanovaleraldehyde and corresponding acetals such as methyl, ethyl and propyl; cyanoamide, and the like.

Hydrocarboxylation reaction solvents which are suitable for use in the extraction process of the present invention include aromatics and substituted aromatics, esters and substituted esters, nitriles and mixtures thereof. Representative solvents include, but are not limited to benzene, toluene, xylenes, methylbenzoate, dimethylbenzoates, methylpropionate, methylbutyrate, methyloctanoate, acetonitrile, propionitrile caprylonitrile, and the like.

It has been found that extraction of the oxygenated cyanocompound product cannot be readily accomplished if the reaction mix contains either an alcohol reaction solvent or a substantial proportion of alcohol in the reaction mix. If the hydrocarboxylation reaction is carried out in an alcohol reaction solvent, the conjugate phase extraction may be carried out if the alcohol is removed by suitable means, such as low temperature distilling or vacuum stripping, and is replaced with a suitable solvent as listed above for the extraction.

The hydrocarboxylation catalyst utilized must be soluble in the reaction solvent utilized. Hydrocarboxylation catalysts capable of being separated by the process of the present invention include Group VIIIB metal carbonyls, preferably cobalt and/or ruthenium carbonyl catalysts.

Catalyst promoter ligand compounds which are compatible with the process of the subject invention include amines, diamines, pyridines and substituted pyridines, pyridine oxide and substituted pyridine oxides, phosphines, phosphine oxides, sulfoxides, arsines and the like.

Extracting liquids which are suitable for use in the present invention are generally liquid hydrocarbons that are at least partially miscible with the reaction solvent utilized. The hydrocarbons should be a poor solvent for the hydrocarboxylation catalyst, however. Suitable extracting liquids include alkanes and alkenes having from 5 to about 20 carbon atoms; preferred are alkanes and alkenes having from 5 to about 8 carbon atoms.

The amount of extracting liquid, or hydrocarbon used in the extraction step should be that amount sufficient to separate substantially all of the catalyst into the reaction solvent phase (which includes the replacement solvent phase in the event an alcohol was used as the reaction solvent and was replaced) and to separate a significant amount of the oxygenated cyanocompound product in the hydrocarbon phase. The volumetric ratio of hydrocarbon to reaction mixture or reactor effluent is generally between 1:1 and about 10:1, and preferably in the range of about 1:1 to about 4:1. As stated above, subsequent treatments with hydrocarbon and/or hydrocarbon/solvent mixtures may be conducted if desired.

The separation may be performed at temperatures sufficient to maintain the extracting liquid solvent and products in the liquid state and catalysts in the solubilized state, yet low enough so that the catalyst is not destroyed. Temperatures between about 28° C. to about 75° C. are preferred. Separation may be carried out at reduced or elevated pressure, and a partial pressure of carbon monoxide is advantageous.

It is necessary, in order to prevent catalyst decomposition, to substantially exclude oxygen from the system. Maximum catalyst recovery is achieved when amounts of unreacted substrates in the reaction mix or reactor effluent are minimized before separation. This is generally accomplished by low temperature distillation or vacuum stripping.

According to the process of the present invention, the hydrocarboxylation catalyst, including promoter ligands, are recovered in a concentrated and active form in the reaction solvent (or replacement solvent) and may be diluted and recycled back to the hydrocarboxylation reaction without the necessity of a reactivation procedure. These hydrocarboxylation catalysts are recovered and may be recycled without significant loss in either activity or selectivity to the products desired.

SPECIFIC EMBODIMENTS OF THE INVENTION

EXAMPLE 1

The hydrocarboxylation of acrylonitrile to form methyl-cyanopropionate was performed in methylbenzoate solvent at a carbon monoxide pressure (5% $H_2$) of 800 psi at a temperature of 97.5° C. The reactor was charged with 100 ml methylbenzoate, 13.5 g acrylonitrile, 9.78 g methanol, 0.75 g 4-picoline and 1.37 g of $Co_2(CO)_8$.

Following the reaction, 142 g of reactor effluent containing 20.6 g methyl-cyanopropionate was added to about 275 ml of hexane. Two conjugate phases developed, and the heavier catalyst-containing reaction solvent layer was separated and treated with 100 ml of a mixture of 22% methylbenzoate, 78% hexane (by volume). Two conjugate phases developed, and the catalyst-containing reaction solvent layer was recovered, diluted to the volume of the original reaction solvent and was recycled to the reactor. The amounts of reactant and reaction conditions were repeated in a second reaction. Results of both reactions are contained in Table 1.

EXAMPLE 2

The hydrocarboxylation of acrylonitrile to form methyl-cyanopropionate was performed in benzene as the reaction solvent at a carbon monoxide pressure (5% $H_2$) of 800 psi at 97.5° C. The reactor was charged with 87.9 g benzene, 13.5 g acrylonitrile, 9.78 g methanol, 0.88 4-picoline-N-oxide, and 1.37 g of cobalt carbonyl.

Following the reaction, 120 ml of reactor effluent was mixed with 120 ml octane and the catalyst-containing reaction solvent layer was recovered. Sixty milliliters octane was added to the catalyst-containing phase, and the catalyst-containing reaction solvent phase was again recovered. Thirty-seven milliliters of a 22% benzene/78% octane volumetric mixture was added to the catalyst-containing phase followed by an addition of 10 ml of octane.

The catalyst-containing layer was recovered, diluted to its original volume and was recycled to the reactor. The promoter ligand compound which had partially precipitated during the separation procedure, was re-added to the reaction solvent, and the amounts of reactant and the reaction conditions of the original run were repeated. The results of the original and recycle reaction runs are reported in Table 1 below.

EXAMPLE 3

The hydrocarboxylation process, separation process, and the recycle hydrocarboxylation process of Example 1 was repeated, with the exception that 0.70 g N,N,N',N', tetramethylpropane diamine was utilized as the promoter ligand compound. Results of the original and recycle test runs are reported in Table 1.

Comparative Example 4

A separation of the hydrocarboxylation catalyst from the cyanocompound product was attempted with an extracting liquid which was immiscible with the reaction solvent. Methyl-cyanopropionate was prepared by the hydrocarboxylation of acrylonitrile with methanol in adiponitrile solvent. Diethylether was used as the extracting liquid, following the procedure of Example 1.

Although about 66% of the cyanoester was extracted using an immiscible extracting liquid, when the catalyst was subjected to a recycle reaction, selectivity for the 3-cyanoester decreased while activity of the cobalt carbonyl catalyst in general decreased substantially. In fact, during the recycle hydrocarboxylation reaction, the catalyst which was separated with the use of an immiscible extracting liquid lost all activity. The results of the original and recycle test runs are reported in Table 1.

Comparative Example 5

Methyl-cyanopropionate was prepared in a hydrocarboxylation reaction of acrylonitrile and methanol in a methanol solution using cobalt carbonyl and 4-picoline-N-oxide using the procedure of Example 1. After two extractions with octane, the cobalt catalyst at least partially precipitated, being converted to an inactive form. Only 3.7% of the cyanoester was extracted from the alcohol reaction solvent, methanol.

EXAMPLE 6

Decyl-cyanoproprionate was prepared by hydrocarboxylation in dimethylphthalate reaction solvent and was extracted from the reaction mixture with octane. About 44% of the cyanoester was extracted, with the cobalt carbonyl catalyst exhibiting about 30% activity in a recycle hydrocarboxylation.

As is demonstrated by the results set forth in Table 1 the separation of hydrocarboxylation catalysts from oxygenated cyanocompound products is accomplished by the process of the present invention yielding high proportions of active catalyst suitable for recycle, with good product separation. As used in the table, the following terms are defined as:

$$\% \text{ Conversion} = \frac{\text{moles nitrile reacted}}{\text{moles nitrile fed}} \times 100$$

$$\% \text{ Selectivity} = \frac{\text{moles specific cyanoester obtained}}{\text{moles nitrile reacted}} \times 100$$

Thus it should be apparent to those skilled in the art that the subject invention accomplishes the objects set forth above. It is to be understood that the subject invention is not to be limited by the examples set forth herein. These have been provided merely to demonstrate operability, and the selection of various extracting liquid and reaction solvent combinations can be determined from the total specification disclosure provided without departing from the spirit of the invention herein disclosed and described, the scope of the invention including modifications and variations that fall within the scope of the attached claims.

TABLE I

Separation of Co $(CO)_8$ From Reaction Mixtures Containing Methyl-Cyanopropionate (CE) and Activity Thereof

| Example No. | % Co Recovered | % CE Extracted | % Conversion Original | % Conversion Recycle | % Selectivity Original | % Selectivity Recycle | Reaction Time[c] (Minutes) Original | Reaction Time[c] (Minutes) Recycle |
|---|---|---|---|---|---|---|---|---|
| 1 | 97.5 | 91 | 100 | 100 | 3CE[a] 35<br>2CE[b] 65 | 38<br>62 | 25 | 26 |
| 2 | 97 | 74.7 | 82.1 | 89.3 | 3CE 43.7<br>2CE 55.5 | 43.1<br>56.9 | 42 | 60 |
| 3[d] | 90 | 60.5 | 100 | 90 | 3CE 100<br>2CE 0 | 95<br>0 | 150 | 90 |
| Comp.4[e] | | 66 | 58.9 | 16.1 | 3CE 74.9<br>2CE 25.1 | 65.4<br>34.6 | 190 | 300 |
| Comp. 5 | — | 3.7 | | — | | | | — |

[a]3CE - 3 methyl - cyanopropionate
[b]2CE - 2 methyl - cyanopropionate
[c] - Batch reaction
[d] - % $H_2$ in synthesis gas - 2.2% original, 5.0% recycle
[e] - Selectivity change due to partial reduction of 4-picoline-N-oxide to 4-picoline

We claim:

1. A process for the separation of a substantially active catalyst containing at least one of cobalt carbonyl and ruthenium carbonyl from an oxygenated cyanocompound product contained in a reaction mixture having a solvent selected from the group aromatics, substituted aromatics, esters, nitriles, and mixtures thereof comprising the steps of:
   - contacting the reaction mixture with an extracting hydrocarbon selected from the group consisting of alkenes or alkanes having from about 5 to about 20 carbon atoms to form a hydrocarbon/solvent conjugate solution, wherein the hydrocarbon is at least partially miscible with the solvent; and,
   - recovering the solvent phase from the hydrocarbon phase of the conjugate solution, whereby said active catalyst remains substantially in the solvent phase.

2. The process of claim 1 wherein the volumetric ratio of hydrocarbon to reaction mixture is about 1:1 to about 10:1.

3. The process of claim 1 wherein the volumetric ratio of hydrocarbon to reaction mixture is about 1:1 to about 4:1.

4. The process of claim 1 wherein the hydrocarbon is an alkane or alkene having from 5 to 8 carbon atoms.

5. The process of claim 1 wherein the hydrocarbon is hexane.

6. The process of claim 1 wherein the hydrocarbon is octane.

7. The process of claim 1 wherein the catalyst is substantially soluble in the solvent.

8. The process of claim 1 wherein the hydrocarbon is a poor solvent for the catalyst.

9. The process of claim 1 wherein the catalyst is cobalt carbonyl.

10. The process of claim 1 wherein the catalyst is ruthenium carbonyl.

11. The process of claim 1 wherein the separation is carried out at a temperature of about 28° C. to about 75° C.

12. The process of claim 1 wherein the oxygenated cyanocompound is selected from the group consisting of cyanoacids, cyanoesters, cyanoaldehydes, cyanoacetals, cyanoamides and mixtures thereof.

13. The process of claim 1 wherein the oxygenated cyanocompound is a hydrocarboxylation derivative of acrylonitrile.

14. The process of claim 1 wherein the oxygenated cyanocompound is methyl-cyanopropionate.

15. The process of claim 1 wherein the solvent is benzene.

16. The process of claim 1 wherein the solvent is methylbenzoate.

17. The process of claim 1 wherein the solvent is an ester.

18. The process of claim 1 wherein the solvent is a nitrile.

19. The process of claim 1 wherein the reaction mixture contains a promoter ligand compound, said promoter ligand compound remaining at least partially in the solvent phase.

20. The process of claim 19 wherein the promoter ligand compound is selected from the group consisting of amines, diamines, pyridines, substituted pyridines, pyridine oxide, substituted pyridine oxides, phosphines, phosphine oxides, sulfoxides, arsines and mixtures thereof.

21. The process of claim 19 wherein the promoter ligand compound is 4-picoline-N-oxide.

22. The process of claim 19 wherein the promoter compound is 4-picoline.

23. The process of claim 19 wherein the promoter ligand compound is N, N, N',N', tetramethylpropane diamine.

24. The process of claim 1 including the step of contacting the hydrocarbon/solvent conjugate solution with a hydrocarbon/solvent mixture.

25. The process of claim 1 including the step of contacting the reaction mixture with a hydrocarbon/solvent mixture comprising at least one of the extracting hydrocarbon or a mixture of the extracting hydrocarbon and the reaction solvent.

26. The process of claim 1 including the steps of contacting the previously separated solvent phase with a hydrocarbon/solvent mixture comprising at least one of the extracting hydrocarbon or a mixture of the extracting hydrocarbon and the reaction solvent.

27. The process of claim 1 wherein oxygen is substantially excluded.

28. The process of claim 1 wherein the separation is carried out under a partial pressure of carbon monoxide.

29. The process of claim 1 wherein unreacted substrates are removed initially.

30. The process of claim 29 wherein said substrates are removed by low temperature distillation.

31. The process of claim 29 wherein said substrates are removed by vacuum stripping.

32. A process for the separation of a substantially active catalyst containing at least one of cobalt carbonyl and ruthenium carbonyl from an oxygenated cyanocompound product contained in a reaction mixture having an alcohol solvent, comprising the steps of:

adding to the reaction mixture a replacement solvent selected from the group aromatics, substituted aromatics, esters, nitriles and mixtures thereof;

removing the alcohol solvent;

contacting the replacement solvent-containing reaction mixture with an extracting hydrocarbon selected from the group consisting of alkanes or alkenes having from about 5 to about 20 carbon atoms to form a hydrocarbon/replacement solvent conjugate solution, wherein the hydrocarbon is at least partially miscible with the replacement solvent; and recovering the replacement solvent phase from the hydrocarbon phase of the conjugate solution, whereby said active catalyst remains substantially in the replacement phase.

33. The process of claim 32 wherein the alcohol solvent is removed by low temperature distillation.

34. The process of claim 32 wherein the alcohol solution is removed by vacuum stripping.

35. The process of claim 32 wherein oxygen is substantially excluded.

36. The process of claim 32 wherein the hydrocarbon is an alkane or alkene having from 5 to 8 carbon atoms.

37. The process of claim 32 wherein the catalyst is cobalt carbonyl.

38. The process of claim 32 wherein the oxygenated cyanocompound is selected from the group consisting of cyanoacids, cyanoesters, cyanoaldehydes, cyanoacetals, cyanoamides and mixtures thereof.

39. The process of claim 32 wherein the oxygenated cyanocompound is a hydrocarboxylation derivative of acrylonitrile.

40. The process of claim 32 wherein the oxygenated cyanocompound is methyl-cyanopropionate.

41. The process of claim 32 wherein the replacement solvent is benzene.

42. The process of claim 32 wherein the replacement solvent is methylbenzoate.

43. The process of claim 32 wherein the reaction mixture contains a promoter ligand compound, said promoter ligand compound remaining at least partially in the replacement solvent phase.

44. The process of claim 43 wherein the promoter ligand compound is selected from the group consisting of amines, diamines, pyridines, substituted pyridines, pyridine oxide, substituted pyridine oxides, phosphines, phosphine oxides, sulfoxides, arsines and mixtures thereof.

45. The process of claim 43 wherein the promoter ligand compound is 4-picoline-N-oxide.

46. The process of claim 43 wherein the promoter ligand compound is 4-picoline.

47. The process of claim 43 wherein the promoter ligand compound is N, N, N',N', tetramethylpropane diamine.

48. The process of claim 32 including the steps of contacting the hydrocarbon/replacement solvent conjugate solution with a hydrocarbon/replacement solvent mixture comprising at least one of the extracting hydrocarbon or a mixture of the extracting hydrocarbon and the replacement solvent.

49. The process of claim 32 including the steps of contacting the non-alcohol replacement solvent containing reaction mixture with a hydrocarbon/replacement solvent mixture comprising at least one of the extracting hydrocarbon or a mixture of the extracting hydrocarbon and the replacement solvent.

50. The process of claim 32 including the steps of contacting the previously separated replacement solvent phase with a hydrocarbon/replacement solvent mixture comprising at least one of the extracting hydrocarbon or a mixture of the extracting hydrocarbon and the replacement solvent.

* * * * *